(12) United States Patent
Strohmann

(10) Patent No.: US 11,580,204 B2
(45) Date of Patent: Feb. 14, 2023

(54) DUAL-FREQUENCY ULTRASONIC SENSOR SYSTEM WITH FREQUENCY SPLITTER

(71) Applicant: QUALCOMM Incorporated, San Diego, CA (US)

(72) Inventor: Jessica Liu Strohmann, Cupertino, CA (US)

(73) Assignee: QUALCOMM Incorporated, San Diego, CA (US)

( * ) Notice: Subject to any disclaimer, the term of this patent is extended or adjusted under 35 U.S.C. 154(b) by 903 days.

(21) Appl. No.: 16/453,898

(22) Filed: Jun. 26, 2019

(65) Prior Publication Data

US 2020/0410070 A1 Dec. 31, 2020

(51) Int. Cl.
| | |
|---|---|
| *G06F 21/32* | (2013.01) |
| *B06B 1/06* | (2006.01) |
| *G01S 7/521* | (2006.01) |
| *H04R 1/24* | (2006.01) |

(52) U.S. Cl.
CPC ............ *G06F 21/32* (2013.01); *B06B 1/0614* (2013.01); *G01S 7/521* (2013.01); *H04R 1/24* (2013.01)

(58) Field of Classification Search
CPC ...................................................... G06F 21/32
See application file for complete search history.

(56) References Cited

U.S. PATENT DOCUMENTS

| | | | |
|---|---|---|---|
| 10,661,309 B2* | 5/2020 | Chaggares | B06B 1/0207 |
| 11,288,479 B2* | 3/2022 | Rasmussen | G06K 19/07354 |
| 2006/0253026 A1 | 11/2006 | Gueck et al. | |
| 2012/0172721 A1 | 7/2012 | Curra et al. | |
| 2012/0267986 A1* | 10/2012 | Galluzzo | B06B 1/0603 310/348 |
| 2017/0246662 A1* | 8/2017 | Kidwell, Jr. | H01L 41/081 |
| 2017/0323131 A1* | 11/2017 | Lu | G06V 40/10 |
| 2017/0344778 A1 | 11/2017 | Lee et al. | |
| 2018/0129849 A1* | 5/2018 | Strohmann | G06F 21/32 |

FOREIGN PATENT DOCUMENTS

WO WO2018151547 A1 8/2018

OTHER PUBLICATIONS

International Search Report and Written Opinion—PCT/US2020/034410—ISA/EPO—Sep. 10, 2020.

* cited by examiner

*Primary Examiner* — Olisa Anwah
(74) *Attorney, Agent, or Firm* — Qualcomm Incorporated

(57) ABSTRACT

An apparatus may include an ultrasonic sensor system having a first layer stack and a second layer stack. The first layer stack may include a first ultrasonic transmitter and the second layer stack may include a second ultrasonic transmitter. The first layer stack and/or the second layer stack may include an ultrasonic receiver. A frequency splitting layer may reside between the first layer stack and the second layer stack.

26 Claims, 12 Drawing Sheets

DUAL-FREQUENCY ULTRASONIC SENSOR SYSTEM WITH FREQUENCY SPLITTER

TECHNICAL FIELD

This disclosure relates generally to sensor devices and related methods, including but not limited to ultrasonic sensor systems and methods for using such systems.

DESCRIPTION OF THE RELATED TECHNOLOGY

Biometric authentication can be an important feature for controlling access to devices, etc. Many existing products include some type of biometric authentication. Although some existing biometric authentication technologies provide satisfactory performance, improved methods and devices would be desirable.

SUMMARY

The systems, methods and devices of the disclosure each have several innovative aspects, no single one of which is solely responsible for the desirable attributes disclosed herein.

One innovative aspect of the subject matter described in this disclosure may be implemented in an apparatus. The apparatus may include an ultrasonic sensor system having a first layer stack and a second layer stack. The first layer stack may include a first ultrasonic transmitter and the second layer stack may include a second ultrasonic transmitter. The first layer stack and/or the second layer stack may include an ultrasonic receiver. In some implementations, a frequency splitting layer resides between the first layer stack and the second layer stack. In some instances, a mobile device may be, or may include, the apparatus. For example, a mobile device may include an apparatus as disclosed herein. According to some examples, a display device may include the apparatus.

In some examples, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

According to some examples, the control system may be configured to control the first ultrasonic transmitter to transmit a first ultrasonic wave. The first ultrasonic wave may include a first frequency. In some examples, the control system may be configured to receive, from the first ultrasonic receiver, first signals corresponding to reflections of the first ultrasonic wave from a surface of a portion of a target object positioned on an outer surface of the apparatus.

According to some implementations, the control system may be configured to perform an authentication process that is based, at least in part, on the first signals. In some examples, the control system may be configured to obtain fingerprint data based on portions of the first signals received within a time interval corresponding with fingerprints.

In some implementations, the control system may be configured to control the second ultrasonic transmitter transmit a second ultrasonic wave through the frequency splitting layer and the first layer stack. The second ultrasonic wave may include a second frequency that is lower than the first frequency.

According to some examples, the frequency splitting layer may have a relatively lower acoustic impedance than that of a first adjacent layer of the first layer stack and a second adjacent layer of the second layer stack, and a thickness that corresponds to a half wavelength of the second frequency. In some implementations, the frequency splitting layer may have a relatively higher acoustic impedance than that of a first adjacent layer of the first layer stack and a second adjacent layer of the second layer stack, and a thickness that corresponds to an odd multiple of a quarter wavelength of the second frequency. In some such implementations, the frequency splitting layer may have a thickness that corresponds to a quarter wavelength of the first frequency.

In some examples, the second layer stack may include a second ultrasonic receiver. In some such examples, the control system may be configured to receive, from the second ultrasonic receiver, second signals corresponding to reflections of the second ultrasonic wave from an interior of the portion of the target object and to perform an authentication process that is based, at least in part, on the second signals. According to some such examples, the second signals may include dermis layer information corresponding to reflections of the second ultrasonic wave received from the portion of the target object within a time interval corresponding with a dermis layer. The authentication process may be based, at least in part, on the dermis layer information. In some examples, the authentication process may be based, at least in part, on both the first signals and the second signals.

In some implementations, the first signals may also correspond to reflections of a harmonic of the second ultrasonic wave from the surface of the portion of the target object. According to some examples, the second signals may also correspond to reflections of a subharmonic of the first ultrasonic wave from the interior of the portion of the target object. In some instances, the first frequency may be in the range of 10 MHz to 20 MHz. In some such examples, the second frequency may be in the range of 1 MHz to 10 MHz.

In some instances, a single piezoelectric layer or a multilayer piezoelectric structure of the first layer stack functions as the first ultrasonic transmitter and the first ultrasonic receiver. According to some examples, the frequency splitting layer may be proximate a first side of the second layer stack. Some such examples may include a high-impedance backing layer proximate a second side of the second layer stack. The backing layer may, for example, have a thickness in the range of 10 to 100 microns.

Other innovative aspects of the subject matter described in this disclosure may be implemented in an apparatus. The apparatus may include an ultrasonic sensor system having a first layer stack and a second layer stack. The first layer stack may include a first ultrasonic transmitter and the second layer stack may include a second ultrasonic transmitter. The first layer stack and/or the second layer stack may include an ultrasonic receiver. In some implementations, a frequency splitting layer resides between the first layer stack and the second layer stack.

In some examples, the apparatus may include a control system. The control system may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof.

According to some examples, the control system may be configured for controlling the first ultrasonic transmitter transmit a first ultrasonic wave through the frequency splitting layer and the second layer stack. The first ultrasonic wave may include a first frequency. In some examples, the control system may be configured for receiving, from the first ultrasonic receiver, first signals corresponding to reflections of the first ultrasonic wave from a surface of a portion of a target object positioned on an outer surface of the apparatus. The outer surface may be on a first side of the second layer stack and the frequency splitting layer may be on a second and opposing side of the second layer stack. According to some examples, the control system may be configured for performing an authentication process that is based, at least in part, on the first signals.

In some implementations, the control system may be configured for controlling the second ultrasonic transmitter transmit a second ultrasonic wave. The second ultrasonic wave may include a second frequency that is lower than the first frequency. In some such implementations, the control system may be configured for receiving, from the first ultrasonic receiver, second signals corresponding to reflections of the second ultrasonic wave from the surface of the portion of the target object. In some instances, the second signals also may correspond to reflections of a harmonic of the second ultrasonic wave.

In some examples, the second layer stack may include a second ultrasonic receiver. The control system may be configured for receiving, from the second ultrasonic receiver, third signals corresponding to reflections of the second ultrasonic wave from an interior of the portion of the target object. The authentication process may be based, at least in part, on the third signals.

Other innovative aspects of the subject matter described in this disclosure may be implemented in a method of controlling an ultrasonic sensor system. In some examples, the method may involve controlling a first ultrasonic transmitter of a first layer stack to transmit a first ultrasonic wave. The first ultrasonic wave may include a first frequency. The method may involve controlling a second ultrasonic transmitter of a second layer stack to transmit a second ultrasonic wave through the first layer stack and through a frequency splitting layer between the first layer stack and the second layer stack. The second ultrasonic wave may include a second frequency that is lower than the first frequency.

The method may involve performing an authentication process that is based, at least in part, on first signals and/or second signals. The first signals may correspond to reflections of the first ultrasonic wave from a surface of a portion of a target object positioned on an outer surface of an apparatus that includes the ultrasonic sensor system. The second signals may correspond to reflections of the second ultrasonic wave from an interior of the portion of the target object.

The method may involve obtaining fingerprint data based on portions of the first signals received within a time interval corresponding with fingerprints. The second signals may, in some examples, include dermis layer information. In some instances, the first signals also correspond to reflections of a harmonic of the second ultrasonic wave from the surface of the portion of the target object. In some examples, the second signals may also correspond to reflections of a subharmonic of the first ultrasonic wave from the interior of the portion of the target object.

In some instances, the first frequency may be in the range of 10 MHz to 20 MHz. The second frequency may, in some examples, be in the range of 1 MHz to 10 MHz.

BRIEF DESCRIPTION OF THE DRAWINGS

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale. Like reference numbers and designations in the various drawings indicate like elements.

DETAILED DESCRIPTION

Figure 1A:
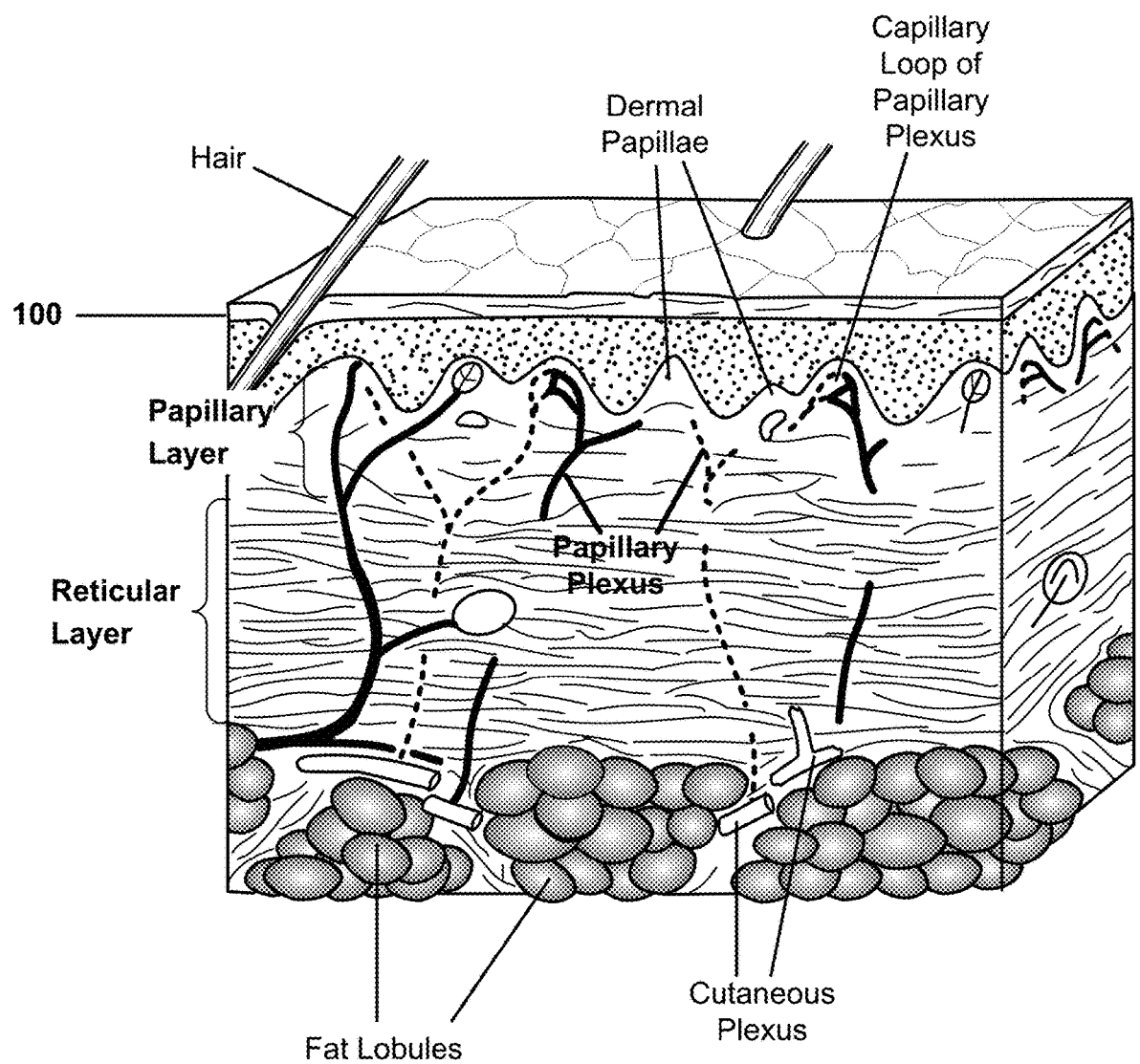
FIG. 1A shows examples of sub-epidermal features.

The following description is directed to certain implementations for the purposes of describing the innovative aspects of this disclosure. However, a person having ordinary skill in the art will readily recognize that the teachings herein may be applied in a multitude of different ways. The described implementations may be implemented in any device, apparatus, or system that includes a biometric system as disclosed herein. In addition, it is contemplated that the described implementations may be included in or associated with a variety of electronic devices such as, but not limited to: mobile telephones, multimedia Internet enabled cellular telephones, mobile television receivers, wireless devices, smartphones, smart cards, wearable devices such as bracelets, armbands, wristbands, rings, headbands, patches, etc., Bluetooth® devices, personal data assistants (PDAs), wireless electronic mail receivers, hand-held or portable computers, netbooks, notebooks, smartbooks, tablets, printers, copiers, scanners, facsimile devices, global positioning system (GPS) receivers/navigators, cameras, digital media players (such as MP3 players), camcorders, game consoles, wrist watches, clocks, calculators, television monitors, flat panel displays, electronic reading devices (e.g., e-readers), mobile health devices, computer monitors, auto displays (including odometer and speedometer displays, etc.), cockpit controls and/or displays, camera view displays (such as the display of a rear view camera in a vehicle), electronic photographs, electronic billboards or signs, projectors, architectural structures, microwaves, refrigerators, stereo systems, cassette recorders or players, DVD players, CD players, VCRs, radios, portable memory chips, washers, dryers, washer/dryers, parking meters, packaging (such as in electromechanical systems (EMS) applications including microelectromechanical systems (MEMS) applications, as well as non-EMS applications), aesthetic structures (such as display of images on a piece of jewelry or clothing) and a variety of EMS devices. The teachings herein also may be used in applications such as, but not limited to, electronic switching devices, radio frequency filters, sensors, accelerometers, gyroscopes, motion-sensing devices, magnetometers, inertial components for consumer electronics, parts of consumer electronics products, steering wheels or other automobile parts, varactors, liquid crystal devices, electrophoretic devices, drive schemes, manufacturing processes and electronic test equipment. Thus, the teachings are not intended to be limited to the implementations depicted solely in the Figures, but instead have wide applicability as will be readily apparent to one having ordinary skill in the art.

Many existing products, including but not limited to mobile phones, are configured for fingerprint-based authentication. However, even premium tier mobile phone manufacturers have had their devices' fingerprint-based authentication systems successfully hacked shortly after product introduction. In some instances, spoofing may involve using a finger-like object that includes silicone rubber, polyvinyl acetate (white glue), gelatin, glycerin, etc., with a fingerprint pattern of a rightful user formed on an outside surface. In some cases, a hacker may form a fingerprint pattern of a rightful user on a sleeve or partial sleeve that can be slipped over or on the hacker's finger.

Authentication methods that are based, at least in part, on sub-epidermal features may be more reliable than those based on fingerprints alone, in part because sub-epidermal features are more difficult to spoof. FIG. 1A shows examples of sub-epidermal features. As used herein, the term "sub-epidermal features" may refer to any of the tissue layers that underlie the epidermis 100, including the dermis, the papillary layer, the reticular layer, the subcutis, etc., and any blood vessels, lymph vessels, sweat glands, hair follicles, hair papilla, fat lobules, etc., that may be present within such tissue layers. Accordingly, sub-epidermal features also may include features not shown in FIG. 1A, such as muscle tissue, bone material, etc.

Accordingly, some disclosed implementations may be configured to perform authentication methods that are based, at least in part, on sub-epidermal features. Some such implementations may include an ultrasonic sensor system that is capable of obtaining image data from the epidermis, such as fingerprint image data, as well as image data that corresponds to sub-epidermal features. Data received from an ultrasonic sensor system may be referred to herein as "ultrasonic image data," "image data," etc., although the data will generally be received from the ultrasonic sensor system in the form of electrical signals. Accordingly, without additional processing such image data would not necessarily be perceivable by a human being as an image.

It can be challenging to design an ultrasonic sensor system that is suitable for imaging both fingerprints and sub-epidermal features. For example, relatively higher frequencies (e.g., 10 MHz or more) are suitable for fingerprint imaging, whereas relatively lower frequencies (e.g., less than 10 MHz) are suitable for imaging sub-epidermal features. If an ultrasonic sensor system is configured to transmit both higher-frequency and lower-frequency ultrasonic waves, "cross-talk" can result.

Some disclosed devices include an ultrasonic sensor system that has a first ultrasonic transmitter in a first layer stack, a second ultrasonic transmitter layer in a second layer stack and a frequency splitting layer between the first layer stack and the second layer stack. In some examples, the first layer stack may be configured for transmitting relatively higher frequencies that are suitable for fingerprint imaging, whereas the second layer stack may be configured for transmitting relatively lower frequencies that are suitable for imaging sub-epidermal features. Such devices may or may not include an ultrasonic receiver in both the first layer stack and the second layer stack, depending on the particular implementation. For example, some implementations may include an ultrasonic receiver in only the first layer stack.

In some examples, the frequency splitting layer may be configured to pass relatively lower frequencies that are suitable for imaging sub-epidermal features. In some such examples, the frequency splitting layer may be configured to suppress relatively higher frequencies that are suitable for fingerprint imaging. In some such implementations, the frequency splitting layer may have a relatively lower acoustic impedance than that of a first adjacent layer of the first layer stack and a second adjacent layer of the second layer stack. According to some such examples, the frequency splitting layer may have a thickness that corresponds to a half wavelength of a frequency that is suitable for imaging sub-epidermal features.

Particular implementations of the subject matter described in this disclosure may be implemented to realize one or more of the following potential advantages. In some examples, the frequency splitting layer may be configured for suppressing cross-talk between the first layer stack and the second layer stack. According to some implementations, the frequency splitting layer may be configured for enhancing the amplitude of a frequency that is suitable for imaging sub-epidermal features.

Figure 1B:
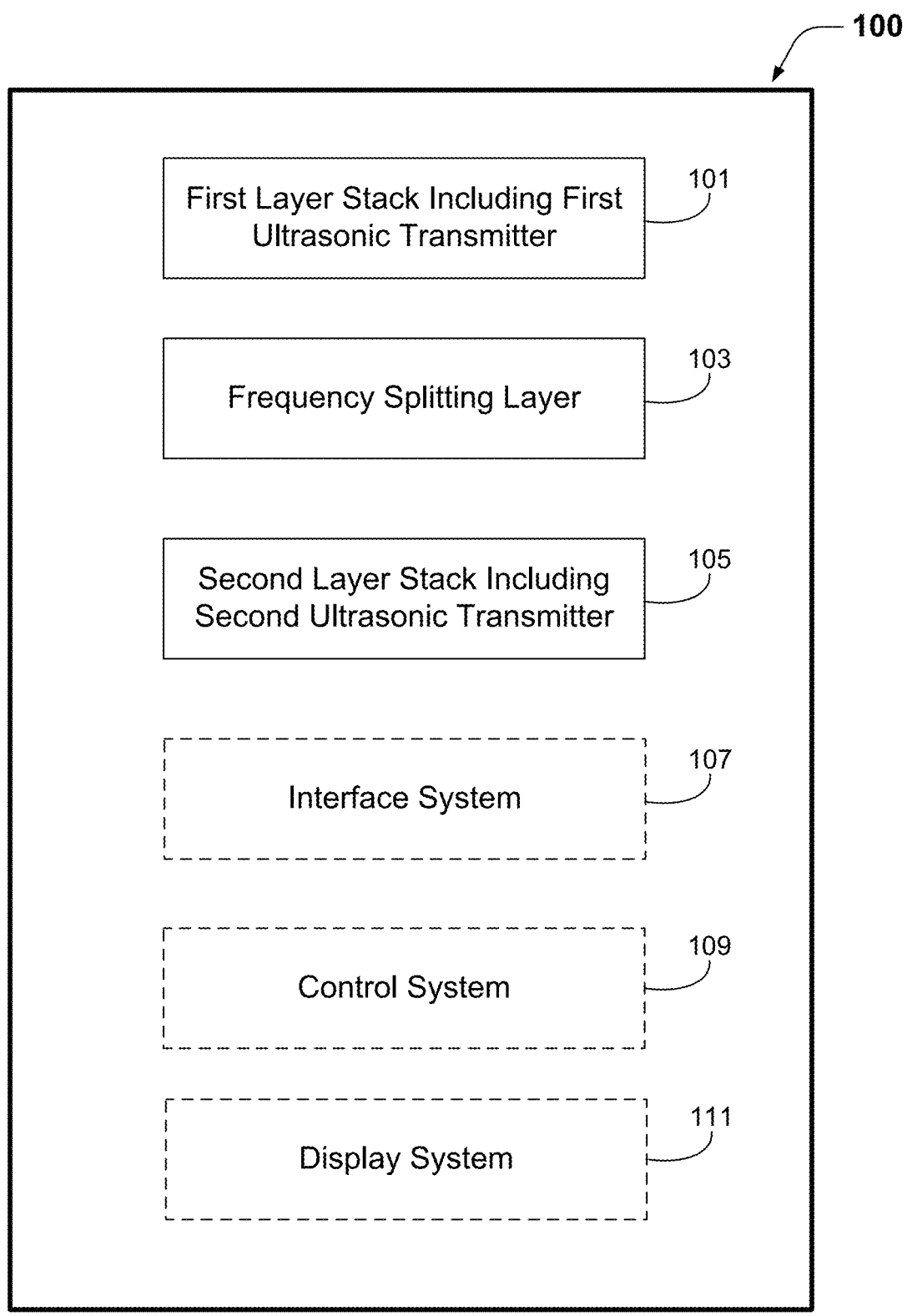
FIG. 1B is a block diagram that shows example components of an apparatus according to some disclosed implementations.

FIG. 1B is a block diagram that shows example components of an apparatus according to some disclosed implementations. As with other disclosed implementations, the numbers, types and arrangements of elements shown in FIG. 1B are merely presented by way of example. Although not shown in FIG. 1B, the apparatus 100 may include other components, such as a cover glass, a sensor substrate, etc. Some examples are described below.

In this implementation, the apparatus 100 includes a first layer stack 101, a frequency splitting layer 103 and a second layer stack 105. The frequency splitting layer 103 may reside between the first layer stack 101 and the second layer stack 105. In this example, the first layer stack 101 includes a first ultrasonic transmitter and the second layer stack 105 includes a second ultrasonic transmitter. The apparatus 100 may or may not include an ultrasonic receiver in both the first layer stack 101 and the second layer stack 105, depending on the particular implementation. For example, some implementations may include an ultrasonic receiver in only the first layer stack 101. According to some implementations, a single piezoelectric layer or a multilayer piezoelectric structure of the first layer stack 101 and/or the second layer stack 105 may function as both an ultrasonic transmitter and an ultrasonic receiver.

For example, in some implementations, the first layer stack 101 and/or the second layer stack 105 may include a piezoelectric layer, such as a layer of PVDF polymer or a layer of PVDF-TrFE copolymer. In some implementations, a separate piezoelectric layer may serve as the ultrasonic transmitter. In some implementations, a single piezoelectric layer may serve as the transmitter and as a receiver. In some implementations, other piezoelectric materials may be used in the piezoelectric layer, such as aluminum nitride (AlN) or lead zirconate titanate (PZT).

The first layer stack 101 and/or the second layer stack 105 may, in some examples, include an array of ultrasonic transducer elements, such as an array of piezoelectric micromachined ultrasonic transducers (PMUTs), an array of capacitive micromachined ultrasonic transducers (CMUTs), etc. In some such examples, a piezoelectric receiver layer, PMUT elements in a single-layer array of PMUTs, or CMUT elements in a single-layer array of CMUTs, may be used as ultrasonic transmitters as well as ultrasonic receivers. According to some alternative examples, the first layer stack 101 and/or the second layer stack 105 may include an ultrasonic plane-wave generator, such as those described below.

In some examples, the frequency splitting layer 103 may include polyethylene terephthalate (PET). In other examples, the frequency splitting layer 103 may include a pressure-sensitive adhesive, a plastic spacer, and/or a metallic tape, such as a copper tape. In some implementations, the frequency splitting layer 103 may be configured to suppress relatively higher-frequency ultrasonic waves that are suitable for fingerprint imaging. According to some such implementations, the relatively higher-frequency ultrasonic waves may be transmitted by the first layer stack 101 and may include a frequency that is referred to herein as a "first frequency." The first frequency may, for example, be in the range of 10 MHz to 20 MHz.

In some examples, the frequency splitting layer 103 may be configured to pass relatively lower-frequency ultrasonic waves that are suitable for imaging sub-epidermal features. According to some such implementations, the relatively lower-frequency ultrasonic waves may be transmitted by the second layer stack 105 and may include a frequency that is referred to herein as a "second frequency." The second frequency may, for example, be in the range of 1 MHz to 10 MHz.

In some implementations, the frequency splitting layer 103 may have a relatively lower acoustic impedance than that of a first adjacent layer of the first layer stack and a second adjacent layer of the second layer stack. According to some such examples, the frequency splitting layer 103 may have a thickness that corresponds to a half wavelength of the second frequency. In some instances, the frequency splitting layer 103 may have a thickness that corresponds to an odd multiple of a quarter wavelength of the first frequency.

However, in some examples the frequency splitting layer 103 may have a relatively higher acoustic impedance than that of a first adjacent layer of the first layer stack and a second adjacent layer of the second layer stack. According to some such examples, the frequency splitting layer 103 may have a thickness that corresponds to an odd multiple of a quarter wavelength of the second frequency.

In some examples, the apparatus 100 may include an interface system 107, a control system 109 and/or a display system 111. The first layer stack 101 may, in some implementations, reside proximate the display system 111, e.g., under the display system 111. In some implementations, the optional display system 111 may be, or may include, a light-emitting diode (LED) display, such as an organic light-emitting diode (OLED) display.

The control system 109 may include one or more general purpose single- or multi-chip processors, digital signal processors (DSPs), application specific integrated circuits (ASICs), field programmable gate arrays (FPGAs) or other programmable logic devices, discrete gates or transistor logic, discrete hardware components, or combinations thereof. The control system 109 also may include (and/or be configured for communication with) one or more memory devices, such as one or more random access memory (RAM) devices, read-only memory (ROM) devices, etc. Accordingly, the apparatus 100 may have a memory system that includes one or more memory devices, though the memory system is not shown in FIG. 1B. The control system 109 may be capable of receiving and processing data from the first layer stack 101 and/or the second layer stack 105, e.g., as described below. In some implementations, functionality of the control system 109 may be partitioned between one or more controllers or processors, such as a dedicated sensor controller and an applications processor of a mobile device.

Some implementations of the apparatus 100 may include an interface system 107. In some examples, the interface system may include a wireless interface system. In some implementations, the interface system may include a user interface system, one or more network interfaces, one or more interfaces between the control system 109 and a memory system and/or one or more interfaces between the control system 109 and one or more external device interfaces (e.g., ports or applications processors).

The interface system 107 may be configured to provide communication (which may include wired or wireless communication, such as electrical communication, radio communication, etc.) between components of the apparatus 100. In some such examples, the interface system 107 may be configured to provide communication between the control system 109 and the first layer stack 101 and/or the second layer stack 105. According to some such examples, a portion of the interface system 107 may couple at least a portion of the control system 109 to the first layer stack 101 and/or the second layer stack 105, e.g., via electrically conducting material.

According to some examples, the interface system 107 may be configured to provide communication between the apparatus 100 and other devices and/or human beings. In some such examples, the interface system 107 may include one or more user interfaces. The interface system 107 may, in some examples, include one or more network interfaces and/or one or more external device interfaces (such as one or more universal serial bus (USB) interfaces). In some implementations, the apparatus 100 may include a memory system. The interface system 107 may, in some examples, include at least one interface between the control system 109 and a memory system.

The apparatus 100 may be used in a variety of different contexts, many examples of which are disclosed herein. For example, in some implementations a mobile device, such as a cell phone, a smart phone, a tablet, a laptop (e.g., a laptop touchpad), etc., may include at least a portion of the apparatus 100. In some implementations, a wearable device may include at least a portion of the apparatus 100. The wearable device may, for example, be a watch, a bracelet, an armband, a wristband, a ring, a headband or a patch. In some implementations, the control system 109 may reside in more than one device. For example, a portion of the control system 109 may reside in a wearable device and another portion of the control system 109 may reside in another device, such as a mobile device (e.g., a smartphone or a tablet computer) and/or a server. The interface system 107 also may, in some examples, reside in more than one device.

Figure 2:
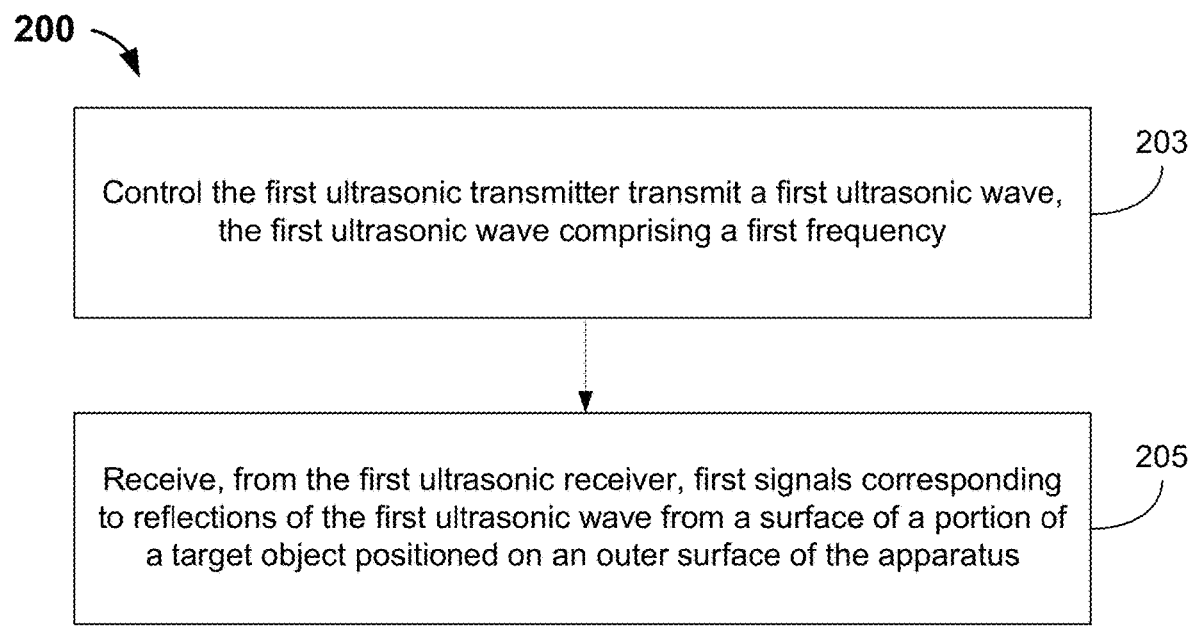
FIG. 2 is a flow diagram that provides examples of operations according to some disclosed methods.

FIG. 2 is a flow diagram that provides examples of operations according to some disclosed methods. The blocks of FIG. 2 may, for example, be performed by the apparatus 100 of FIG. 1B, or by a similar apparatus. As with other methods disclosed herein, the method outlined in FIG. 2 may include more or fewer blocks than indicated. Moreover, the blocks of methods disclosed herein are not necessarily performed in the order indicated.

In this example, block 203 involves controlling a first ultrasonic transmitter of an ultrasonic sensor system to transmit a first ultrasonic wave. In this example, a first layer stack, such as the first layer stack 101 of FIG. 1B, includes the first ultrasonic transmitter. Here, the first ultrasonic wave includes a first frequency. The first frequency may, for example, be within a range of frequencies that are suitable for fingerprint imaging. In some examples, the first frequency may be in the range of 10 MHz to 20 MHz. However, in other examples the first frequency may include frequencies above 20 MHz and/or below 10 MHz.

According to this implementation, block 205 involves receiving, from the first ultrasonic receiver, first signals corresponding to reflections of the first ultrasonic wave from a surface of a portion of a target object positioned on an outer surface of an apparatus that includes the ultrasonic sensor system. If the target object is a finger, the first signals may correspond to reflections of the first ultrasonic wave from a surface of the finger. (As used herein, the term "finger" may refer to any digit, including a thumb. Accordingly, a thumbprint will be considered a type of "fingerprint.") In some examples, method 200 may involve performing an authentication process that is based, at least in part, on the first signals.

According to some implementations, method 200 may involve obtaining fingerprint data based on portions of the first signals received within a time interval corresponding with fingerprints. The time interval may, for example, be measured relative to a time at which the first ultrasonic wave is transmitted. Obtaining the fingerprint data may, for example, involve extracting, via a control system, first target object features from the first signals. The first target object features may, for example, comprise fingerprint features. According to some examples, the fingerprint features may include fingerprint minutiae, keypoints and/or sweat pores. In some examples, the fingerprint features may include ridge ending information, ridge bifurcation information, short ridge information, ridge flow information, island information, spur information, delta information, core information, etc.

In some examples, method 200 may involve performing an authentication process that is based, at least in part, on the fingerprint features. In some examples, block 209 may involve comparing the fingerprint features with fingerprint features of an authorized user. The fingerprint features of the authorized user may, for example, have been received during a previous enrollment process.

In some examples, the control system may be configured for controlling access to the apparatus, or to another device, based at least in part on the authentication process. For example, in some implementations a mobile device (such as a cell phone) may include the apparatus. In some such examples, the control system may be configured for controlling access to the mobile device based, at least in part, on the authentication process.

In some implementations an Internet of things (IoT) device may include the apparatus 100. For example, in some such implementations a device intended for use in a home, such as a remote control device (such as a remote control device for a smart television), a stove, an oven, a refrigerator, a stove, a coffee maker, an alarm system, a door lock, a mail/parcel box lock, a thermostat, etc., may include the apparatus 100. In some such examples, the control system may be configured for controlling access to the IoT device based, at least in part, on the first authentication process.

In alternative implementations, an automobile (including but not limited to a partially or fully autonomous automobile), a partially or fully autonomous delivery vehicle, a drone, or another device typically used outside of the home may include the apparatus 100. In some such examples, the control system may be configured for controlling access to the vehicle, the drone, etc., based at least in part on the first authentication process.

In some examples, including but not limited to many IoT implementations, there may be a metal, plastic, ceramic or polymer layer between an outer surface of the apparatus 100, or an outer surface of a device that includes the apparatus 100, and the first layer stack 101 and/or the second layer stack 105. In such implementations, the acoustic waves from a finger or other target may need to pass through the metal layer before reaching the first layer stack 101 and/or the second layer stack 105. Ultrasound and other acoustic waves can be successfully transmitted through a metal layer, whereas some other types of waves (e.g., light waves) cannot. Similarly, ultrasound and other acoustic waves can be successfully transmitted through an optically opaque plastic, ceramic or polymer layer, whereas some other types of waves, such as light waves, cannot. This feature is another potential advantage of some disclosed implementations, as compared to devices that rely upon optical or capacitive fingerprint sensors.

Figure 3A:
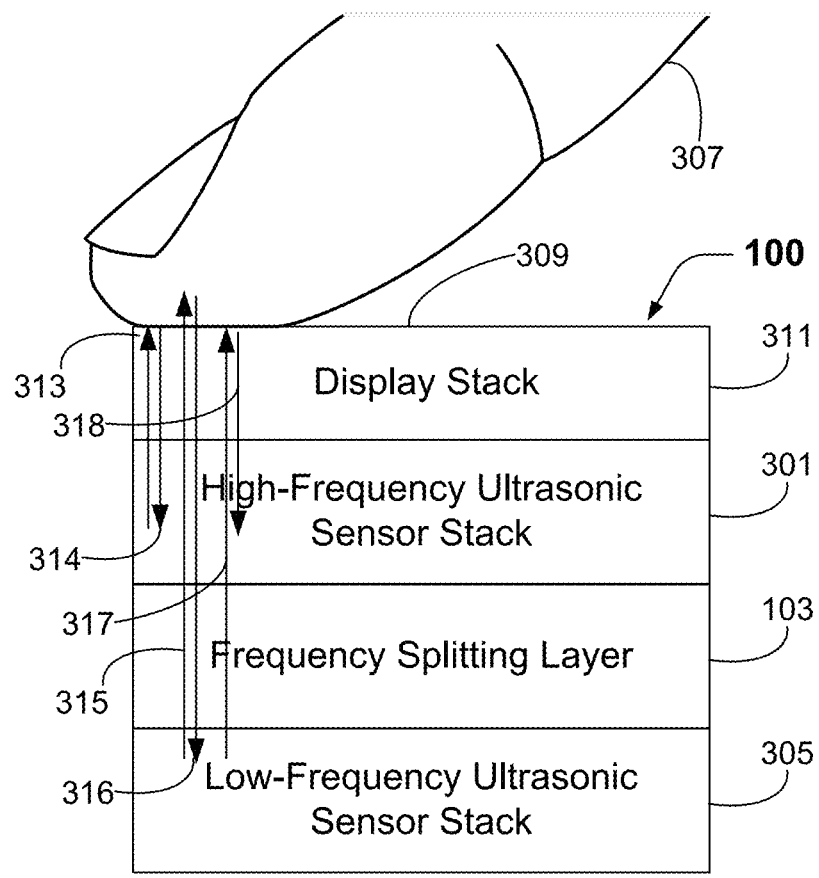
FIG. 3A shows an example of a target object in contact with an outer surface of a device that includes the apparatus shown in FIG. 1B.

FIG. 3A shows an example of a target object in contact with an outer surface of a device that includes the apparatus shown in FIG. 1B. In this example, the target object 307 is a finger, which is in contact with the outer surface 309 of a display stack 311. The display stack 311 may be an instance of the display system 111 of FIG. 1B. In alternative examples, the target object 307 may be in contact with the outer surface of a platen, which may or may not be transparent to visible light.

Here, the apparatus 100 of FIG. 3A includes a high-frequency ultrasonic sensor stack 301, a frequency splitting layer 103 and a low-frequency ultrasonic sensor stack 305. According to this implementation, the high-frequency ultrasonic sensor stack 301 is an instance of the first layer stack 101 shown in FIG. 1B and the low-frequency ultrasonic sensor stack 305 is an instance of the second layer stack 105 shown in FIG. 1B. As with other disclosed implementations, the types, number and arrangement of elements, as well as the dimensions of elements, are merely examples. In some implementations, for example, the high-frequency ultrasonic sensor stack 301 may occupy a different (e.g., smaller) area than the low-frequency ultrasonic sensor stack 305.

In this example, the apparatus 100 is configured to perform the operations of method 200. The arrow 313 shown in FIG. 3A corresponds to the first ultrasonic wave that includes a first frequency, which is described above with reference to block 203 of FIG. 2. The arrow 314 corresponds to the reflections of the first ultrasonic wave from a surface of a portion of a target object positioned on an outer surface of the apparatus.

According to this example, method 200 also involves controlling, via a control system (not shown), an ultrasonic transmitter of the low-frequency ultrasonic sensor stack 305 to transmit a second ultrasonic wave (represented in FIG. 3A by the arrow 315) through the frequency splitting layer 103 and the high-frequency ultrasonic sensor stack 301. The second ultrasonic wave may include a second frequency that is lower than the first frequency referenced above in the discussion of block 203. The second frequency may be in a range of ultrasonic frequencies that a suitable for imaging sub-epidermal features. For example, the second frequency may be in the range of 1 MHz to 10 MHz. In some implementations, the second frequency may be in the range of 2 MHz to 7 MHz.

In some examples, the low-frequency ultrasonic sensor stack 305 may include a second ultrasonic receiver. The control system may be configured to receive, from the second ultrasonic receiver, second signals corresponding to reflections of the second ultrasonic wave (represented in FIG. 3A by the arrow 316) from an interior of the portion of the target object 307. In some such examples, the control system may be configured to perform an authentication process that is based, at least in part, on the second signals. The second signals may, for example, include dermis layer information corresponding to reflections of the second ultrasonic wave received from the portion of the target object 307. The dermis layer information may have been obtained within a time interval corresponding with a dermis layer. The authentication process may be based, at least in part, on the dermis layer information. According to some implementations, the authentication process may be based, at least in part, on both the first signals and the second signals.

Alternatively, or additionally, the second signals may include information regarding other sub-epidermal layers, such as the papillary layer, the reticular layer, the subcutis, etc., and any blood vessels, lymph vessels, sweat glands, hair follicles, hair papilla, fat lobules, etc., that may be present within such tissue layers. Some examples are described above with reference to FIG. 1A. However, the second signals may include information regarding sub-epidermal features that are not shown in FIG. 1A, such as muscle tissue, bone material, etc.

According to some examples, the first signals may also correspond to reflections of a harmonic of the second ultrasonic wave (represented in FIG. 3A by the arrow 318) from the surface of the target object 307. Alternatively, or additionally, the second signals may also correspond to reflections of a subharmonic of the first ultrasonic wave from the interior of the portion of the target object 307.

Figure 3B:
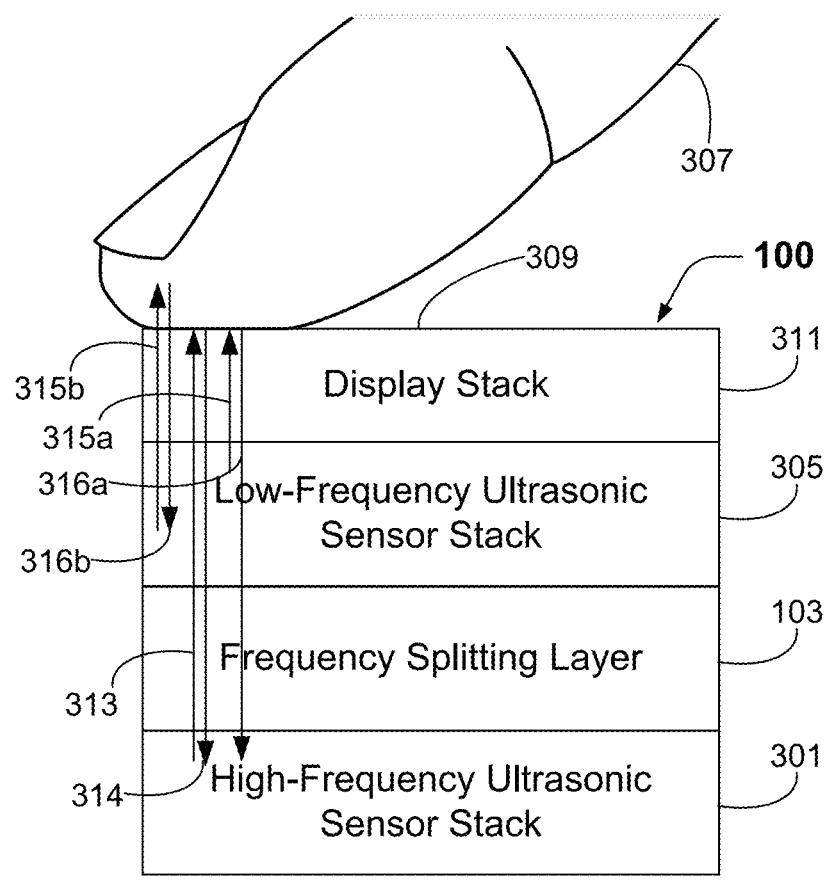
FIG. 3B shows another example of a target object in contact with an outer surface of a device that includes the apparatus shown in FIG. 1B.

FIG. 3B shows an example of a target object in contact with an outer surface of another device that includes the apparatus shown in FIG. 1B. As with other disclosed implementations, the types, number and arrangement of elements, as well as the dimensions of elements, are merely examples. In some implementations, for example, the high-frequency ultrasonic sensor stack 301 may occupy a different (e.g., smaller) area than the low-frequency ultrasonic sensor stack 305. In this example, the target object 307 is a finger, which is in contact with the outer surface 309 of a display stack 311. The display stack 311 may be an instance of the display system 111 of FIG. 1B. In alternative examples, the target object 307 may be in contact with the outer surface of a platen, which may or may not be transparent to visible light.

Like the apparatus 100 of FIG. 3A, the apparatus 100 of FIG. 3B also includes a high-frequency ultrasonic sensor stack 301, a frequency splitting layer 103 and a low-frequency ultrasonic sensor stack 305. However, according to this implementation, the low-frequency ultrasonic sensor stack 305 is "above" the high-frequency ultrasonic sensor stack 301 when viewed as shown in FIG. 3B. Put another way, the outer surface 309 is on a first side of the low-frequency ultrasonic sensor stack 305 and the frequency splitting layer 103 is on a second and opposing side of the low-frequency ultrasonic sensor stack 305. One could also say that the display stack 311 is on a first side of the low-frequency ultrasonic sensor stack 305 and the frequency splitting layer 103 is on a second and opposing side of the low-frequency ultrasonic sensor stack 305.

In this example, the apparatus 100 is configured to perform additional examples of method 200. The arrow 313 shown in FIG. 3A corresponds to an example of the first ultrasonic wave that includes a first frequency, which is described above with reference to block 203 of FIG. 2. In this example, the first ultrasonic wave propagates through the frequency splitting layer 103 and the low-frequency ultrasonic sensor stack 305 before reaching the target object. The arrow 314 corresponds to an example of the reflections of the first ultrasonic wave from the surface of a portion of the target object 307 positioned on an outer surface 309 of the apparatus.

According to this example, method 200 also involves controlling, via a control system (not shown), an ultrasonic transmitter of the low-frequency ultrasonic sensor stack 305 to transmit a second ultrasonic wave (represented in FIG. 3B by the arrows 315a and 315b). The second ultrasonic wave may include a second frequency that is lower than the first frequency referenced above in the discussion of block 203. The second frequency may be in a range of ultrasonic frequencies that a suitable for imaging sub-epidermal features. For example, the second frequency may be in the range of 1 MHz to 10 MHz. In some implementations, the second frequency may be in the range of 2 MHz to 7 MHz.

At least a portion of the second ultrasonic wave (e.g., as represented by the arrow 316a in FIG. 3B) may be reflected from the surface of a portion of the target object 307. At least a portion of these reflected waves may propagate through the frequency splitting layer 103 and may be received by a receiver of the high-frequency ultrasonic sensor stack 301. According to some examples, at least a portion of these reflected waves may include a harmonic of the second ultrasonic wave.

In some examples, the low-frequency ultrasonic sensor stack 305 may include a second ultrasonic receiver. The control system may be configured to receive, from the second ultrasonic receiver, third signals corresponding to reflections of the second ultrasonic wave (represented in FIG. 3A by the arrow 316b) from an interior of the portion of the target object 307. In some such examples, the control system may be configured to perform an authentication process that is based, at least in part, on the third signals. The third signals may, for example, include dermis layer information corresponding to reflections of the second ultrasonic wave received from the portion of the target object 307. The dermis layer information may have been obtained within a time interval corresponding with a dermis layer. The authentication process may be based, at least in part, on the dermis layer information. According to some implementations, the authentication process may be based, at least in part, on the first signals, the second signals and the third signals.

Alternatively, or additionally, the third signals may include information regarding other sub-epidermal layers, such as the papillary layer, the reticular layer, the subcutis, etc., and any blood vessels, lymph vessels, sweat glands, hair follicles, hair papilla, fat lobules, etc., that may be present within such tissue layers. Some examples are described above with reference to FIG. 1A. However, the third signals may include information regarding sub-epidermal features that are not shown in FIG. 1A, such as muscle tissue, bone material, etc.

Figure 4:
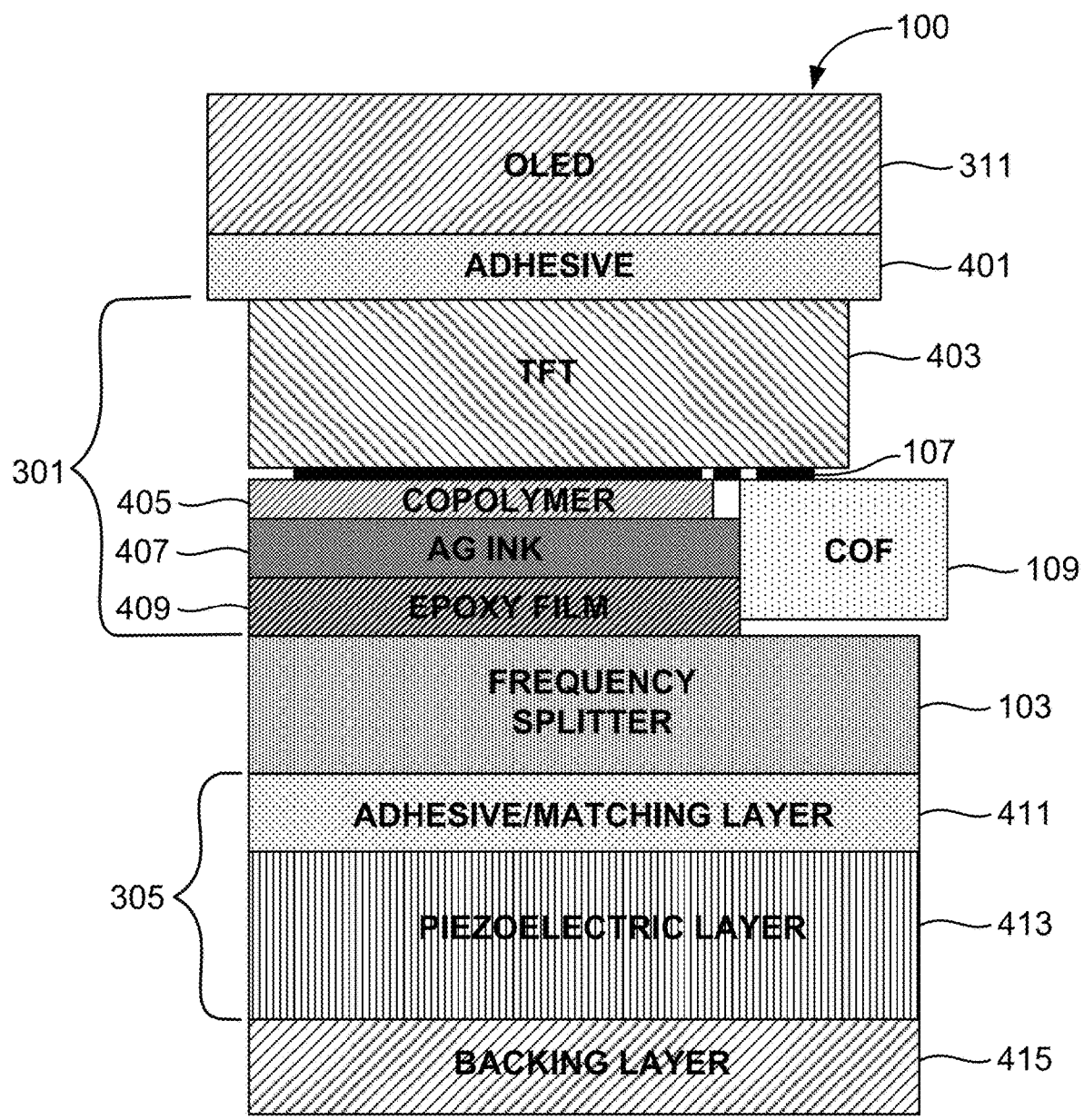
FIG. 4 shows example components of an apparatus according to some disclosed implementations.

FIG. 4 shows example components of an apparatus according to some disclosed implementations. As with other disclosed implementations, the types, number and arrangement of elements, as well as the dimensions of elements, are merely examples. According to this example, the apparatus 100 is configured to perform at least some of the methods disclosed herein. In this example, the display stack 311 includes an OLED display and is attached to the high-frequency ultrasonic sensor stack 301 via an adhesive layer 401.

According to this implementation, the high-frequency ultrasonic sensor stack 301 includes a thin-film transistor (TFT) layer 403 that is coupled to at least a portion of the control system 109 and an upper portion of the piezoelectric layer 405 via a portion of the interface system 107, which includes electrically conducting material. In this implementation, the piezoelectric layer 405 includes one or more piezoelectric polymers. In this example, the interface system 107 also includes a silver ink layer 407 that provides electrical conductivity between the portion of the control system 109 and a lower portion of the piezoelectric layer 405. Although not shown in FIG. 4, a portion of the interface system 107 also provides electrical conductivity between the portion of the control system 109 and the low-frequency ultrasonic sensor stack 305.

In this example, an epoxy film 409 couples the high-frequency ultrasonic sensor stack 301 to the frequency splitting layer 103 and an adhesive layer 411 couples the low-frequency ultrasonic sensor stack 305 to the frequency splitting layer 103. In some implementations, the frequency splitting layer 103 may have a relatively lower acoustic impedance than those of the epoxy film 409 and the adhesive layer 411. In some such implementations, the frequency splitting layer 103 may have a thickness that corresponds to a half wavelength of a frequency (referred to elsewhere herein as "the second frequency") of ultrasonic waves that are transmitted by the ultrasonic transceiver 413.

However, in some examples the frequency splitting layer 103 may have a relatively higher acoustic impedance than those of the epoxy film 409 and the adhesive layer 411. In some such implementations, the frequency splitting layer 103 may have a thickness that corresponds to an odd multiple of a quarter wavelength of the second frequency of ultrasonic waves that are transmitted by the ultrasonic transceiver 413.

In the example, shown in FIG. 4, the apparatus 100 includes a backing layer 415. In this example, the backing layer 415 is configured to absorb energy in order to mitigate or avoid signal interference. According to this example, the frequency splitting layer 103 is proximate a first side of the low-frequency ultrasonic sensor stack 305 and the backing layer 415 is proximate a second side of the low-frequency ultrasonic sensor stack 305. In this example, the backing layer 415 has a higher acoustic impedance than that of the second side of the low-frequency ultrasonic sensor stack 305. In some implementations, the backing layer 415 may have a thickness that is in the range of 10 to 100 microns. In this instance, the backing layer 415 includes tungsten.

Figure 5A:
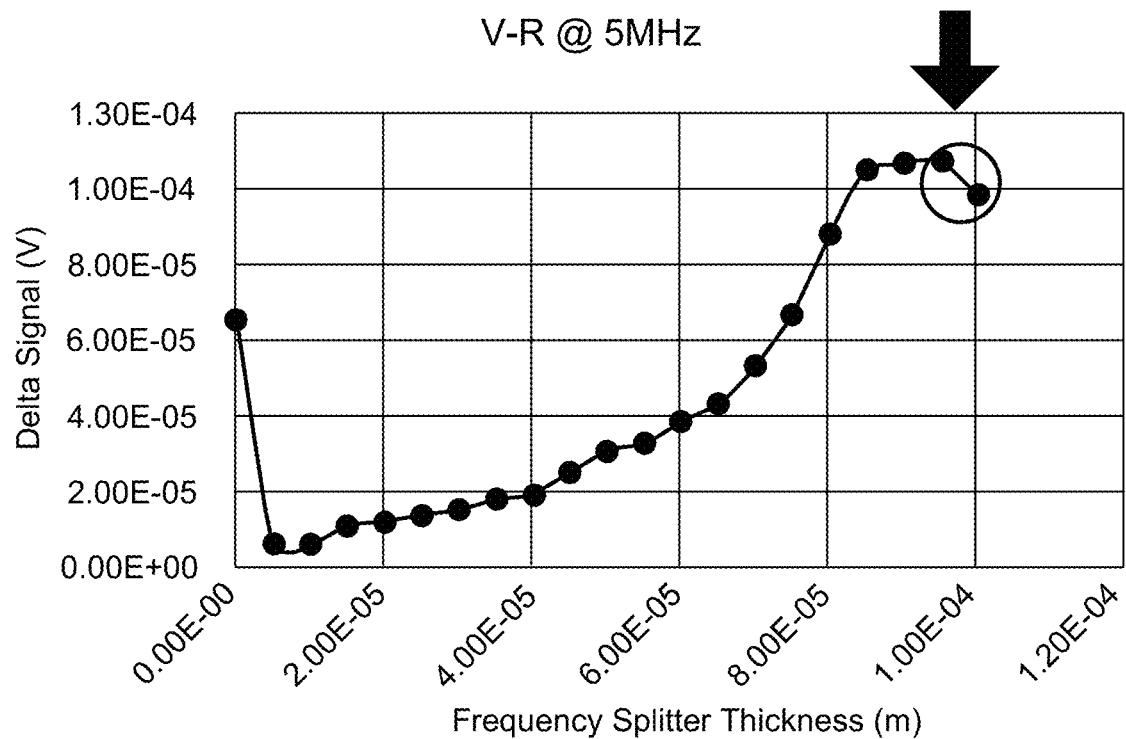
FIGS. 5A and 5B are graphs of delta signal strengths versus frequency splitter thicknesses according to two examples.
Figure 5B:
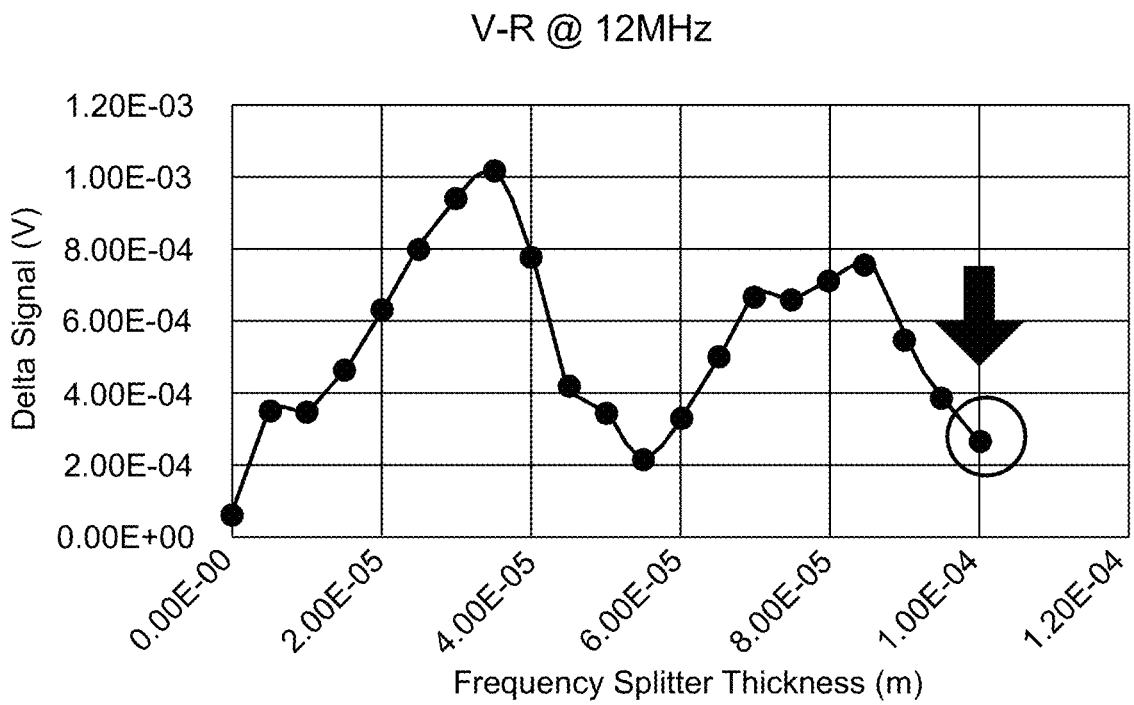

FIGS. 5A and 5B are graphs of delta signal strengths versus frequency splitter thicknesses according to two examples. In each example, the frequency splitter is composed of two-part epoxy. In the examples shown in FIGS. 5A and 5B, the delta signal strengths indicate the differences between signals corresponding to fingerprint ridges (shown as "R" in FIGS. 5A and 5B) and signals corresponding to fingerprint valleys (shown as "V" in FIGS. 5A and 5B). In the example of FIG. 5A the ultrasonic waves were transmitted at 5 MHz (an example of the "second frequency"), whereas in the example of FIG. 5B the ultrasonic waves were transmitted at 12 MHz (an example of the "first frequency"). By comparing FIGS. 5A and 5B, one may observe that the same frequency splitter thickness ($10^{-4}$ meters) that corresponds with a high delta signal strength for the 5 MHz signal also greatly suppresses the 12 MHz signal.

Figure 6:
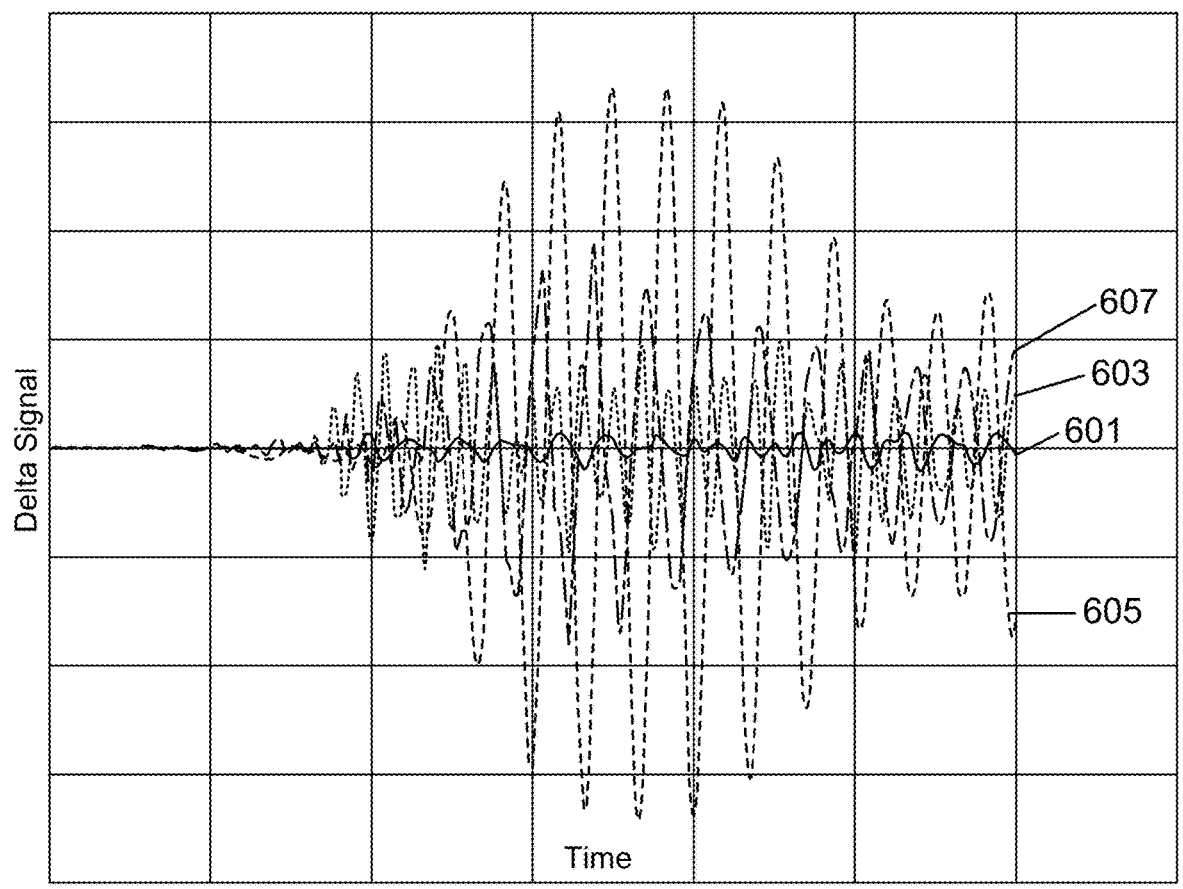
FIG. 6 is a graph that shows examples of delta signal enhancement that may be achieved by some implementations of the disclosed ultrasonic sensor systems.

FIG. 6 is a graph that shows examples of delta signal enhancement that may be achieved by some implementations of the disclosed ultrasonic sensor systems. Each example corresponds to an implementation having an upper ultrasonic sensor stack, a lower ultrasonic sensor stack and a frequency splitting layer between the two ultrasonic sensor stacks, e.g., as described above with reference to FIG. 1B. In this example, the frequency splitting layer is composed of epoxy. In various implementations that were investigated, the epoxy layer varied from 5 microns to 150 microns. According to this example, the signals 601 correspond to reflections received after transmitting 5.5 MHz ultrasonic waves only from the upper ultrasonic sensor stack and the signals 603 correspond to reflections received after transmitting 12 MHz ultrasonic waves only from the upper ultrasonic sensor stack. The 12 MHz ultrasonic waves may, for example, be used for fingerprint imaging and the 5.5 MHz ultrasonic waves may be used for sub-epidermal imaging, such as dermal imaging. Here, the signals 601 and the signals 603 correspond to baseline (BL) signals.

In this example, the signals 605 correspond to reflections received after transmitting 5.5 MHz ultrasonic waves from the upper and lower ultrasonic sensor stacks and the signals 607 correspond to reflections received after transmitting 12 MHz ultrasonic waves from the upper and lower ultrasonic sensor stacks. By comparing the signals 603 with the signals 607, one may see that the delta signal amplitude is approximately doubled for a fingerprint image (@12 MHz), as compared to the delta signal amplitude of the baseline signals. By comparing the signals 601 with the signals 605, one may see that the delta signal amplitude is as much as 20× for subdermal imaging (@5.5 MHz), as compared to the delta signal amplitude of the baseline signals.

Figure 7:
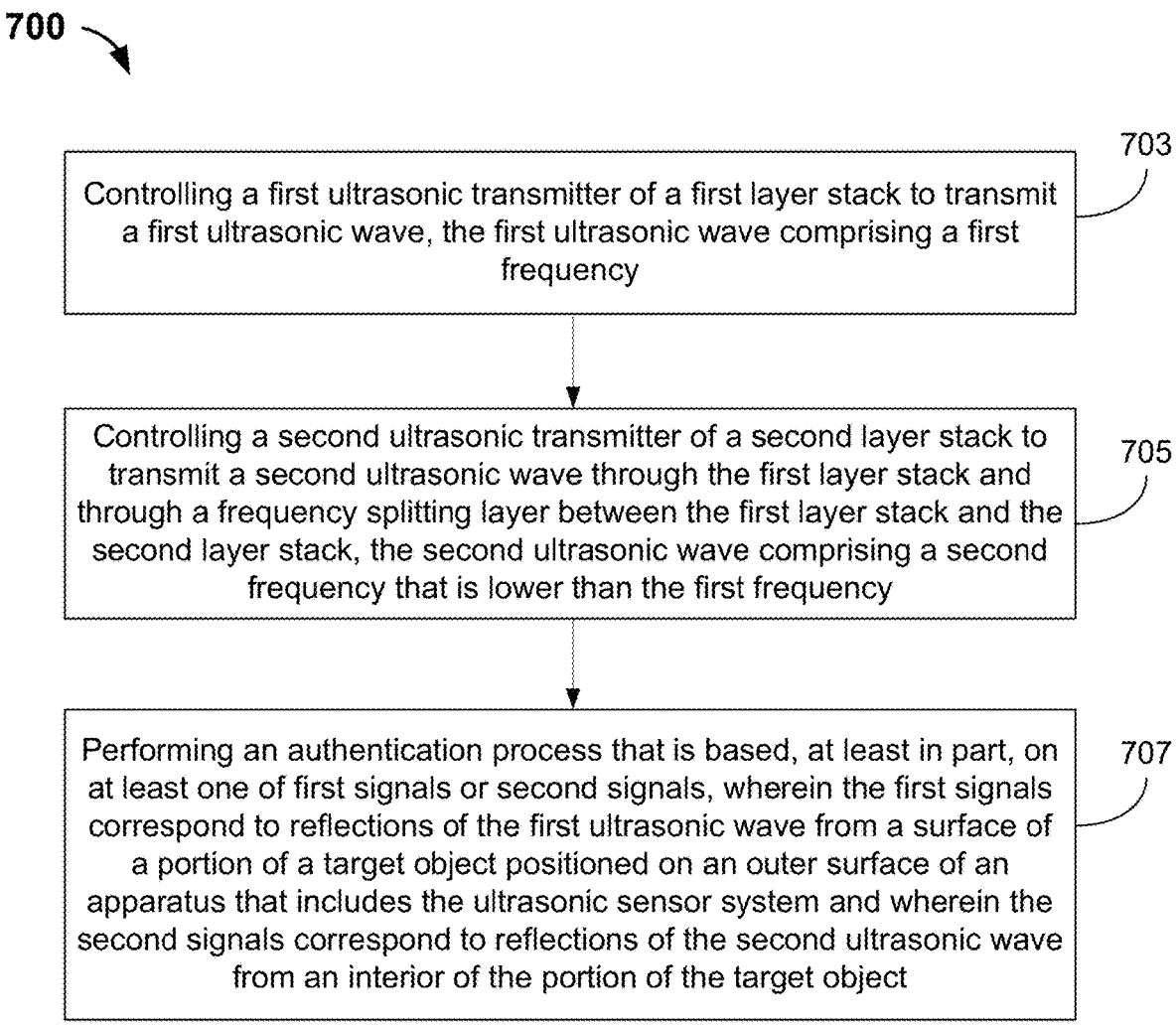
FIG. 7 is a flow diagram that provides examples of operations according to some disclosed methods.

FIG. 7 is a flow diagram that provides examples of operations according to some disclosed methods. The blocks of FIG. 7 may, for example, be performed by the apparatus 100 of FIG. 1B, 3 or 4, or by a similar apparatus. As with other methods disclosed herein, the method outlined in FIG. 7 may include more or fewer blocks than indicated. Moreover, the blocks of methods disclosed herein are not necessarily performed in the order indicated.

In this example, block 703 involves controlling a first ultrasonic transmitter of an ultrasonic sensor system to transmit a first ultrasonic wave. In this example, a first layer stack, such as the first layer stack 101 of FIG. 1B, includes the first ultrasonic transmitter. Here, the first ultrasonic wave includes a first frequency. The first frequency may, for example, be within a range of frequencies that are suitable for fingerprint imaging. In some examples, the first frequency may be in the range of 10 MHz to 20 MHz. However, in other examples the first frequency may include frequencies above 20 MHz and/or below 10 MHz.

According to this example, block 705 involves controlling a second ultrasonic transmitter of the ultrasonic sensor system to transmit a second ultrasonic wave through the first layer stack and through a frequency splitting layer between the first layer stack and the second layer stack. In this example, a second layer stack, such as the second layer stack 105 of FIG. 1B, includes the second ultrasonic transmitter. Here, the second ultrasonic wave includes a second frequency that is lower than the first frequency. The second frequency may, for example, be within a range of frequencies that are suitable for sub-epidermal imaging, such as dermal imaging. In some examples, the second frequency may be in the range of 1 MHz to 10 MHz. However, in other examples the first frequency may include frequencies above 10 MHz and/or below 1 MHz.

In this example, block 707 involves performing an authentication process that is based, at least in part, on at least one of first signals or second signals. In this example, the first signals correspond to reflections of the first ultrasonic wave from a surface of a portion of a target object positioned on an outer surface of an apparatus that includes the ultrasonic sensor system. Here, the second signals correspond to reflections of the second ultrasonic wave from an interior of the portion of the target object. The second signals may, for example, include dermis layer information.

In some examples, method 700 may involve obtaining fingerprint data based on portions of the first signals received within a time interval corresponding with fingerprints. According to some examples, the first signals also may correspond to reflections of a harmonic of the second ultrasonic wave from the surface of the portion of the target object. In some instances, the second signals also may correspond to reflections of a subharmonic of the first ultrasonic wave from the interior of the portion of the target object.

Figure 8:
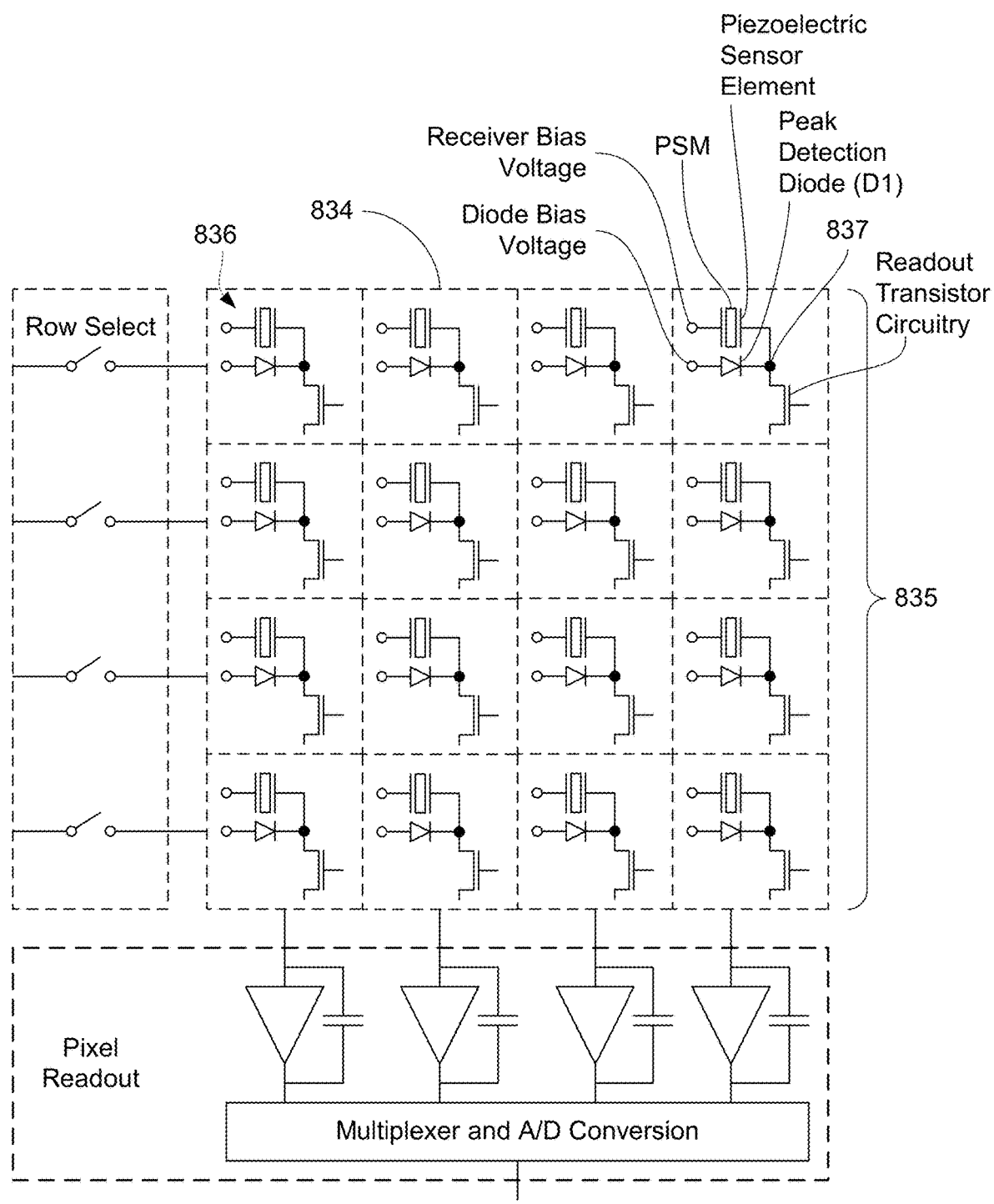
FIG. 8 representationally depicts aspects of a 4×4 pixel array of sensor pixels for an ultrasonic sensor system.

FIG. 8 representationally depicts aspects of a 4×4 pixel array of sensor pixels for an ultrasonic sensor system. Each pixel 834 may be, for example, associated with a local region of piezoelectric sensor material (PSM), a peak detection diode (D1) and a readout transistor (M3); many or all of these elements may be formed on or in a substrate to form the pixel circuit 836. In practice, the local region of piezoelectric sensor material of each pixel 834 may transduce received ultrasonic energy into electrical charges. The peak detection diode D1 may register the maximum amount of charge detected by the local region of piezoelectric sensor material PSM. Each row of the pixel array 835 may then be scanned, e.g., through a row select mechanism, a gate driver, or a shift register, and the readout transistor M3 for each column may be triggered to allow the magnitude of the peak charge for each pixel 834 to be read by additional circuitry, e.g., a multiplexer and an A/D converter. The pixel circuit 836 may include one or more TFTs to allow gating, addressing, and resetting of the pixel 834.

Each pixel circuit 836 may provide information about a small portion of the object detected by the ultrasonic sensor system. While, for convenience of illustration, the example shown in FIG. 8 is of a relatively coarse resolution, ultrasonic sensors having a resolution on the order of 500 pixels per inch or higher may be configured with an appropriately scaled structure. The detection area of the ultrasonic sensor system may be selected depending on the intended object of detection. For example, the detection area may range from about 5 mm×5 mm for a single finger to about 3 inches×3 inches for four fingers. Smaller and larger areas, including square, rectangular and non-rectangular geometries, may be used as appropriate for the target object.

Figure 9A:
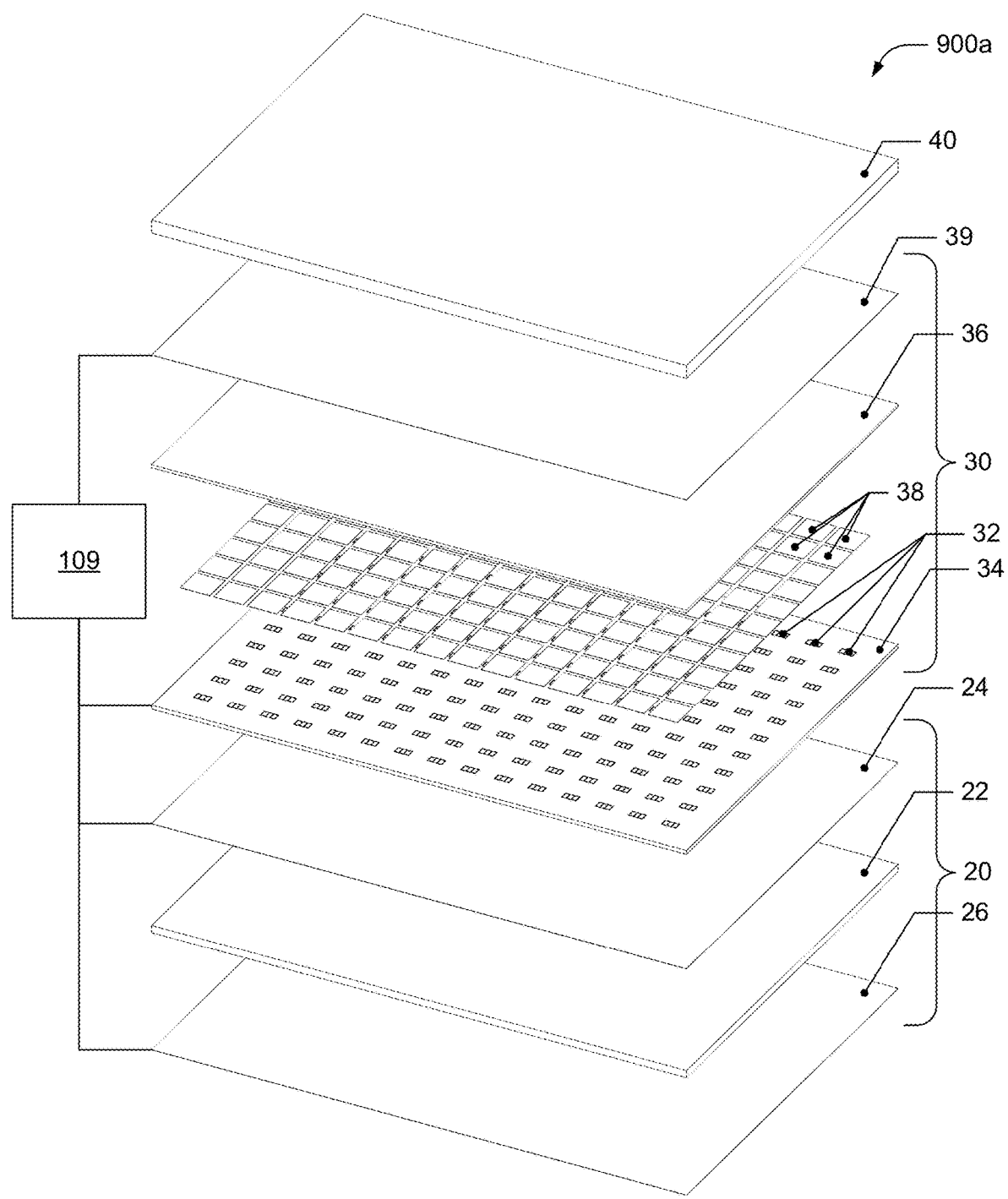
FIG. 9A shows an example of an exploded view of an ultrasonic sensor system.

FIG. 9A shows an example of an exploded view of an ultrasonic sensor system. In this example, the ultrasonic sensor system 900a includes an ultrasonic transmitter 20 and an ultrasonic receiver 30 under a platen 40. According to some implementations, the ultrasonic receiver 30 may be an example of the acoustic receiver system 102 that is shown in FIG. 1 and described above. In some implementations, the ultrasonic transmitter 20 may be an example of the optional ultrasonic transmitter 108 that is shown in FIG. 1 and described above. However, some implementations of the ultrasonic sensor system 900a (and some implementations of the ultrasonic sensor system 900b that is described below with reference to FIG. 9B) do not include the ultrasonic transmitter 20. In some such implementations, the ultrasonic receiver 30 may be configured as an ultrasonic transceiver.

However, in the example shown in FIG. 9A, the ultrasonic transmitter 20 includes a substantially planar piezoelectric transmitter layer 22 and may be capable of functioning as a plane wave generator. Ultrasonic waves may be generated by applying a voltage to the piezoelectric layer to expand or contract the layer, depending upon the signal applied, thereby generating a plane wave. In this example, the control system 109 may be capable of causing a voltage that may be applied to the planar piezoelectric transmitter layer 22 via a first transmitter electrode 24 and a second transmitter electrode 26. In this fashion, an ultrasonic wave may be made by changing the thickness of the layer via a piezoelectric effect. This ultrasonic wave may travel towards a finger (or other object to be detected), passing through the platen 40. A portion of the wave not absorbed or transmitted by the object to be detected may be reflected so as to pass back through the platen 40 and be received by at least a portion of the ultrasonic receiver 30. The first and second transmitter electrodes 24 and 26 may be metallized electrodes, for example, metal layers that coat opposing sides of the piezoelectric transmitter layer 22.

The ultrasonic receiver 30 may include an array of sensor pixel circuits 32 disposed on a substrate 34, which also may be referred to as a backplane, and a piezoelectric receiver layer 36. In some implementations, each sensor pixel circuit 32 may include one or more TFT elements, electrical interconnect traces and, in some implementations, one or more additional circuit elements such as diodes, capacitors, and the like. Each sensor pixel circuit 32 may be configured to convert an electric charge generated in the piezoelectric receiver layer 36 proximate to the pixel circuit into an electrical signal. Each sensor pixel circuit 32 may include a pixel input electrode 38 that electrically couples the piezoelectric receiver layer 36 to the sensor pixel circuit 32.

In the illustrated implementation, a receiver bias electrode 39 is disposed on a side of the piezoelectric receiver layer 36 proximal to platen 40. The receiver bias electrode 39 may be a metallized electrode and may be grounded or biased to control which signals may be passed to the array of sensor pixel circuits 32. Ultrasonic energy that is reflected from the exposed (top) surface of the platen 40 may be converted into localized electrical charges by the piezoelectric receiver layer 36. These localized charges may be collected by the pixel input electrodes 38 and passed on to the underlying sensor pixel circuits 32. The charges may be amplified or buffered by the sensor pixel circuits 32 and provided to the control system 109.

The control system 109 may be electrically connected (directly or indirectly) with the first transmitter electrode 24 and the second transmitter electrode 26, as well as with the receiver bias electrode 39 and the sensor pixel circuits 32 on the substrate 34. In some implementations, the control system 109 may operate substantially as described above.

For example, the control system 109 may be capable of processing the amplified signals received from the sensor pixel circuits 32.

The control system 109 may be capable of controlling the ultrasonic transmitter 20 and/or the ultrasonic receiver 30 to obtain ultrasonic image data, e.g., by obtaining fingerprint images. Whether or not the ultrasonic sensor system 900a includes an ultrasonic transmitter 20, the control system 109 may be capable of obtaining attribute information from the ultrasonic image data. In some examples, the control system 109 may be capable of controlling access to one or more devices based, at least in part, on the attribute information. The ultrasonic sensor system 900a (or an associated device) may include a memory system that includes one or more memory devices. In some implementations, the control system 109 may include at least a portion of the memory system. The control system 109 may be capable of obtaining attribute information from ultrasonic image data and storing the attribute information in the memory system. In some implementations, the control system 109 may be capable of capturing a fingerprint image, obtaining attribute information from the fingerprint image and storing attribute information obtained from the fingerprint image (which may be referred to herein as fingerprint image information) in the memory system. According to some examples, the control system 109 may be capable of capturing a fingerprint image, obtaining attribute information from the fingerprint image and storing attribute information obtained from the fingerprint image even while maintaining the ultrasonic transmitter 20 in an "off" state.

In some implementations, the control system 109 may be capable of operating the ultrasonic sensor system 900a in an ultrasonic imaging mode or a force-sensing mode. In some implementations, the control system may be capable of maintaining the ultrasonic transmitter 20 in an "off" state when operating the ultrasonic sensor system in a force-sensing mode. The ultrasonic receiver 30 may be capable of functioning as a force sensor when the ultrasonic sensor system 900a is operating in the force-sensing mode. In some implementations, the control system 109 may be capable of controlling other devices, such as a display system, a communication system, etc. In some implementations, the control system 109 may be capable of operating the ultrasonic sensor system 900a in a capacitive imaging mode.

The platen 40 may be any appropriate material that can be acoustically coupled to the receiver, with examples including plastic, ceramic, sapphire, metal and glass. In some implementations, the platen 40 may be a cover plate, e.g., a cover glass or a lens glass for a display. Particularly when the ultrasonic transmitter 20 is in use, fingerprint detection and imaging can be performed through relatively thick platens if desired, e.g., 3 mm and above. However, for implementations in which the ultrasonic receiver 30 is capable of imaging fingerprints in a force detection mode or a capacitance detection mode, a thinner and relatively more compliant platen 40 may be desirable. According to some such implementations, the platen 40 may include one or more polymers, such as one or more types of parylene, and may be substantially thinner. In some such implementations, the platen 40 may be tens of microns thick or even less than 10 microns thick.

Examples of piezoelectric materials that may be used to form the piezoelectric receiver layer 36 include piezoelectric polymers having appropriate acoustic properties, for example, an acoustic impedance between about 2.5 MRayls and 5 MRayls. Specific examples of piezoelectric materials that may be employed include ferroelectric polymers such as polyvinylidene fluoride (PVDF) and polyvinylidene fluoride-trifluoroethylene (PVDF-TrFE) copolymers. Examples of PVDF copolymers include 60:40 (molar percent) PVDF-TrFE, 70:30 aPVDF-TrFE, 80:20 PVDF-TrFE, and 90:10 PVDR-TrFE. Other examples of piezoelectric materials that may be employed include polyvinylidene chloride (PVDC) homopolymers and copolymers, polytetrafluoroethylene (PTFE) homopolymers and copolymers, and diisopropylammonium bromide (DIPAB).

The thickness of each of the piezoelectric transmitter layer 22 and the piezoelectric receiver layer 36 may be selected so as to be suitable for generating and receiving ultrasonic waves. In one example, a PVDF planar piezoelectric transmitter layer 22 is approximately 28 μm thick and a PVDF-TrFE receiver layer 36 is approximately 12 μm thick. Example frequencies of the ultrasonic waves may be in the range of 5 MHz to 30 MHz, with wavelengths on the order of a millimeter or less.

Figure 9B:
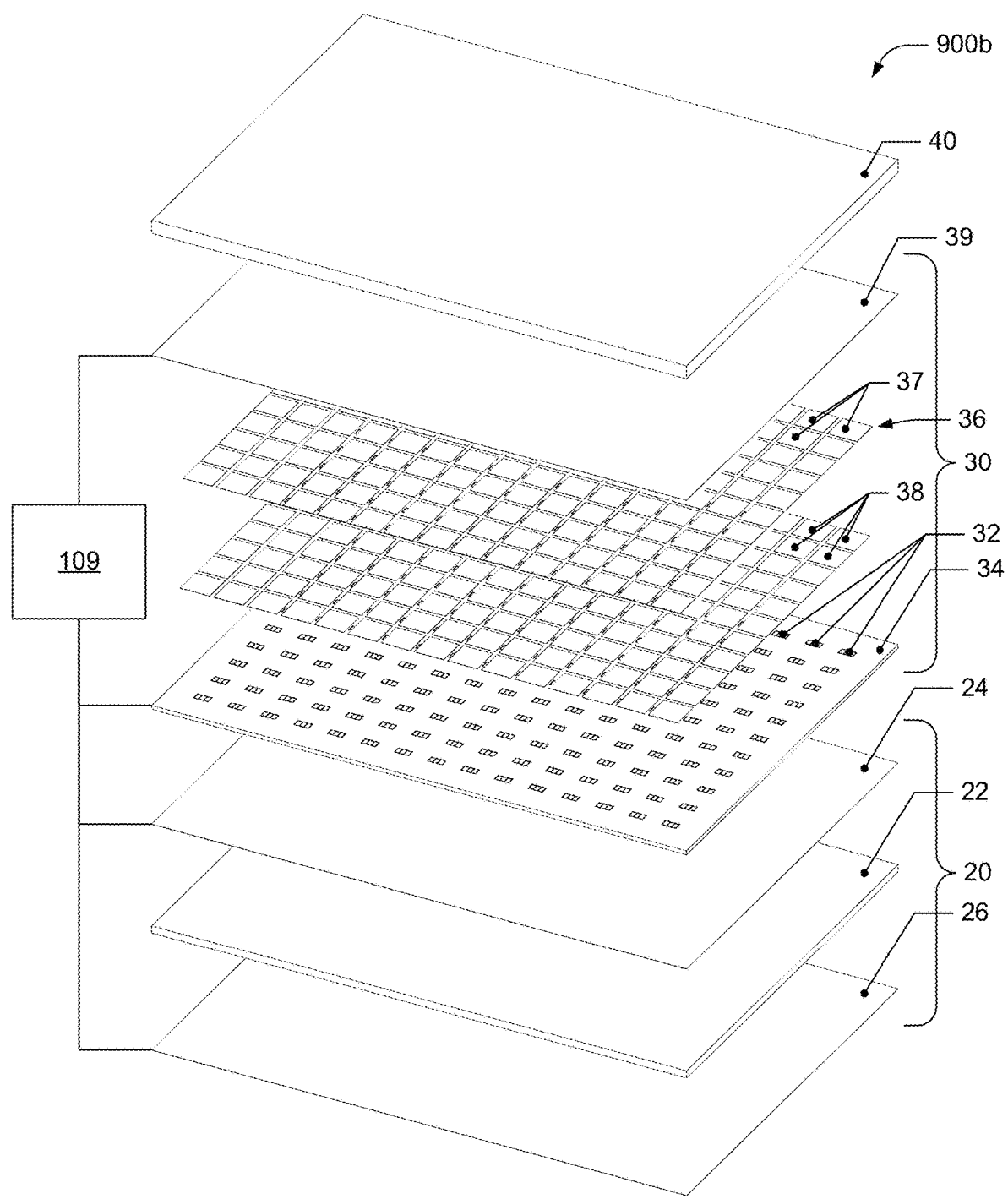
FIG. 9B shows an exploded view of an alternative example of an ultrasonic sensor system.

FIG. 9B shows an exploded view of an alternative example of an ultrasonic sensor system. In this example, the piezoelectric receiver layer 36 has been formed into discrete elements 37. In the implementation shown in FIG. 9B, each of the discrete elements 37 corresponds with a single pixel input electrode 38 and a single sensor pixel circuit 32. However, in alternative implementations of the ultrasonic sensor system 900b, there is not necessarily a one-to-one correspondence between each of the discrete elements 37, a single pixel input electrode 38 and a single sensor pixel circuit 32. For example, in some implementations there may be multiple pixel input electrodes 38 and sensor pixel circuits 32 for a single discrete element 37.

FIGS. 9A and 9B show example arrangements of ultrasonic transmitters and receivers in an ultrasonic sensor system, with other arrangements being possible. For example, in some implementations, the ultrasonic transmitter 20 may be above the ultrasonic receiver 30 and therefore closer to the object(s) to be detected. In some implementations, the ultrasonic transmitter may be included with the ultrasonic sensor array (e.g., a single-layer transmitter and receiver). In some implementations, the ultrasonic sensor system may include an acoustic delay layer. For example, an acoustic delay layer may be incorporated into the ultrasonic sensor system between the ultrasonic transmitter 20 and the ultrasonic receiver 30. An acoustic delay layer may be employed to adjust the ultrasonic pulse timing, and at the same time electrically insulate the ultrasonic receiver 30 from the ultrasonic transmitter 20. The acoustic delay layer may have a substantially uniform thickness, with the material used for the delay layer and/or the thickness of the delay layer selected to provide a desired delay in the time for reflected ultrasonic energy to reach the ultrasonic receiver 30. In doing so, the range of time during which an energy pulse that carries information about the object by virtue of having been reflected by the object may be made to arrive at the ultrasonic receiver 30 during a time range when it is unlikely that energy reflected from other parts of the ultrasonic sensor system is arriving at the ultrasonic receiver 30. In some implementations, the substrate 34 and/or the platen 40 may serve as an acoustic delay layer.

As used herein, a phrase referring to "at least one of" a list of items refers to any combination of those items, including single members. As an example, "at least one of: a, b, or c" is intended to cover: a, b, c, a-b, a-c, b-c, and a-b-c.

The various illustrative logics, logical blocks, modules, circuits and algorithm processes described in connection with the implementations disclosed herein may be implemented as electronic hardware, computer software, or combinations of both. The interchangeability of hardware and software has been described generally, in terms of functionality, and illustrated in the various illustrative components, blocks, modules, circuits and processes described above. Whether such functionality is implemented in hardware or software depends upon the particular application and design constraints imposed on the overall system.

The hardware and data processing apparatus used to implement the various illustrative logics, logical blocks, modules and circuits described in connection with the aspects disclosed herein may be implemented or performed with a general purpose single- or multi-chip processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, or, any conventional processor, controller, microcontroller, or state machine. A processor also may be implemented as a combination of computing devices, e.g., a combination of a DSP and a microprocessor, a plurality of microprocessors, one or more microprocessors in conjunction with a DSP core, or any other such configuration. In some implementations, particular processes and methods may be performed by circuitry that is specific to a given function.

In one or more aspects, the functions described may be implemented in hardware, digital electronic circuitry, computer software, firmware, including the structures disclosed in this specification and their structural equivalents thereof, or in any combination thereof. Implementations of the subject matter described in this specification also may be implemented as one or more computer programs, i.e., one or more modules of computer program instructions, encoded on a computer storage media for execution by, or to control the operation of, data processing apparatus.

If implemented in software, the functions may be stored on or transmitted over as one or more instructions or code on a computer-readable medium, such as a non-transitory medium. The processes of a method or algorithm disclosed herein may be implemented in a processor-executable software module which may reside on a computer-readable medium. Computer-readable media include both computer storage media and communication media including any medium that may be enabled to transfer a computer program from one place to another. Storage media may be any available media that may be accessed by a computer. By way of example, and not limitation, non-transitory media may include RAM, ROM, EEPROM, CD-ROM or other optical disk storage, magnetic disk storage or other magnetic storage devices, or any other medium that may be used to store desired program code in the form of instructions or data structures and that may be accessed by a computer. Also, any connection may be properly termed a computer-readable medium. Disk and disc, as used herein, includes compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

Various modifications to the implementations described in this disclosure may be readily apparent to those having ordinary skill in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "exemplary" is used exclusively herein, if at all, to mean "serving as an example, instance, or illustration." Any implementation described herein as "exemplary" is not necessarily to be construed as preferred or advantageous over other implementations.

Certain features that are described in this specification in the context of separate implementations also may be implemented in combination in a single implementation. Conversely, various features that are described in the context of a single implementation also may be implemented in multiple implementations separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems may generally be integrated together in a single software product or packaged into multiple software products. Additionally, other implementations are within the scope of the following claims. In some cases, the actions recited in the claims may be performed in a different order and still achieve desirable results.

It will be understood that unless features in any of the particular described implementations are expressly identified as incompatible with one another or the surrounding context implies that they are mutually exclusive and not readily combinable in a complementary and/or supportive sense, the totality of this disclosure contemplates and envisions that specific features of those complementary implementations may be selectively combined to provide one or more comprehensive, but slightly different, technical solutions. It will therefore be further appreciated that the above description has been given by way of example only and that modifications in detail may be made within the scope of this disclosure.

The invention claimed is:

1. An apparatus comprising:
   an ultrasonic sensor system, comprising:
   a first ultrasonic transmitter in a first layer stack of the ultrasonic sensor system, the first layer stack including a first ultrasonic receiver;
   a second ultrasonic transmitter layer in a second layer stack of the ultrasonic sensor system, the second layer stack including a second ultrasonic receiver; and
   a frequency splitting layer between the first layer stack and the second layer stack; and a control system configured to:

control the first ultrasonic transmitter to transmit a first ultrasonic wave, the first ultrasonic wave comprising a first frequency;

receive, from the first ultrasonic receiver, first signals corresponding to reflections of the first ultrasonic wave from a surface of a portion of a target object positioned on an outer surface of the apparatus;

control the second ultrasonic transmitter transmit a second ultrasonic wave through the frequency splitting layer and the first layer stack, the second ultrasonic wave comprising a second frequency that is lower than the first frequency;

receive, from the second ultrasonic receiver, second signals corresponding to reflections of the second ultrasonic wave from an interior of the portion of the target object; and perform an authentication process that is based, at least in part, on the second signals.

2. The apparatus of claim 1, wherein the control system is configured to perform an authentication process that is based, at least in part, on the first signals.

3. The apparatus of claim 1, wherein the control system is configured to obtain fingerprint data based on portions of the first signals received within a time interval corresponding with fingerprints.

4. The apparatus of claim 1, wherein the frequency splitting layer has a relatively lower acoustic impedance than that of a first adjacent layer of the first layer stack and a second adjacent layer of the second layer stack, and a thickness that corresponds to a half wavelength of the second frequency.

5. The apparatus of claim 1, wherein the frequency splitting layer has a relatively higher acoustic impedance than that of a first adjacent layer of the first layer stack and a second adjacent layer of the second layer stack, and a thickness that corresponds to an odd multiple of a quarter wavelength of the second frequency.

6. The apparatus of claim 5, wherein the frequency splitting layer has a thickness that corresponds to a quarter wavelength of the first frequency.

7. The apparatus of claim 1, wherein the second signals comprise dermis layer information corresponding to reflections of the second ultrasonic wave received from the portion of the target object within a time interval corresponding with a dermis layer.

8. The apparatus of claim 1, wherein the authentication process is based, at least in part, on the dermis layer information.

9. The apparatus of claim 1, wherein the authentication process is based, at least in part, on both the first signals and the second signals.

10. The apparatus of claim 1, wherein the first signals also correspond to reflections of a harmonic of the second ultrasonic wave from the surface of the portion of the target object.

11. The apparatus of claim 1, wherein the second signals also correspond to reflections of a subharmonic of the first ultrasonic wave from the interior of the portion of the target object.

12. The apparatus of claim 1, wherein the first frequency is in the range of 10 MHz to 20 MHz and wherein the second frequency is in the range of 1 MHz to 10 MHz.

13. The apparatus of claim 1, wherein a single piezoelectric layer or a multilayer piezoelectric structure of the first layer stack functions as the first ultrasonic transmitter and the first ultrasonic receiver.

14. The apparatus of claim 1, wherein the frequency splitting layer is proximate a first side of the second layer stack, further comprising a high-impedance backing layer proximate a second side of the second layer stack.

15. The apparatus of claim 14, wherein the backing layer has a thickness in the range of 10 to 100 microns.

16. An apparatus comprising:
an ultrasonic sensor system, comprising:
a first ultrasonic transmitter in a first layer stack of the ultrasonic sensor system, the first layer stack including a first ultrasonic receiver;
a second ultrasonic transmitter layer in a second layer stack of the ultrasonic sensor system; and
a frequency splitting layer, the frequency splitting layer residing between the first layer stack and the second layer stack; and
a control system configured to:
control the first ultrasonic transmitter transmit a first ultrasonic wave through the means for frequency splitting and the second layer stack, the first ultrasonic wave comprising a first frequency;
receive, from the first ultrasonic receiver, first signals corresponding to reflections of the first ultrasonic wave from a surface of a portion of a target object positioned on an outer surface of the apparatus, the outer surface being on a first side of the second layer stack and the means for frequency splitting being on a second and opposing side of the second layer stack; and
perform an authentication process that is based, at least in part, on the first signals.

17. The apparatus of claim 16, wherein the control system is configured to control the second ultrasonic transmitter transmit a second ultrasonic wave, the second ultrasonic wave comprising a second frequency that is lower than the first frequency.

18. The apparatus of claim 17, wherein the control system is configured to receive, from the first ultrasonic receiver, second signals corresponding to reflections of the second ultrasonic wave from the surface of the portion of the target object.

19. The apparatus of claim 17, wherein the second signals also correspond to reflections of a harmonic of the second ultrasonic wave.

20. The apparatus of claim 17, wherein the second layer stack includes a second ultrasonic receiver and wherein the control means comprises means for receiving, from the second ultrasonic receiver, third signals corresponding to reflections of the second ultrasonic wave from an interior of the portion of the target object, wherein the authentication process is based, at least in part, on the third signals.

21. A method of controlling an ultrasonic sensor system, the method comprising:
controlling a first ultrasonic transmitter of a first layer stack to transmit a first ultrasonic wave, the first ultrasonic wave comprising a first frequency;
controlling a second ultrasonic transmitter of a second layer stack to transmit a second ultrasonic wave through the first layer stack and through a frequency splitting layer between the first layer stack and the second layer stack, the second ultrasonic wave comprising a second frequency that is lower than the first frequency; and
performing an authentication process that is based, at least in part, on at least one of first signals or second signals, wherein the first signals correspond to reflections of the first ultrasonic wave from a surface of a portion of a target object positioned on an outer surface of an apparatus that includes the ultrasonic sensor system and wherein the second signals correspond to reflections of the second ultrasonic wave from an interior of the portion of the target object.

22. The method of claim 21, further comprising obtaining fingerprint data based on portions of the first signals received within a time interval corresponding with fingerprints.

23. The method of claim 21, wherein the second signals comprise dermis layer information.

24. The method of claim 21, wherein the first signals also correspond to reflections of a harmonic of the second ultrasonic wave from the surface of the portion of the target object.

25. The method of claim 21, wherein the second signals also correspond to reflections of a subharmonic of the first ultrasonic wave from the interior of the portion of the target object.

26. The method of claim 21, wherein the first frequency is in the range of 10 MHz to 20 MHz and wherein the second frequency is in the range of 1 MHz to 10 MHz.

* * * * *